United States Patent
D'Orazio et al.

(10) Patent No.: US 8,242,168 B2
(45) Date of Patent: Aug. 14, 2012

(54) USE OF PHTHALIDE DERIVATIVES FOR THE TREATMENT OF TYPE 2 DIABETES MELLITUS

(75) Inventors: Daniel D'Orazio, Halten (CH); Antoine De Saizieu, Brunstatt (FR); Goede Schueler, Eimeldingen (DE); Daniel Raederstorff, Brunstatt (FR); Sandra Renata Teixeira, Brookline, MA (US); Ying Wang Schmidt, Basel (CH); Peter Weber, Malsburg-Marzell (DE); Swen Wolfram, Waldshut-Tiengen (DE)

(73) Assignee: DSM IP Assets B.V., Heerlen (NL)

( * ) Notice: Subject to any disclaimer, the term of this patent is extended or adjusted under 35 U.S.C. 154(b) by 473 days.

(21) Appl. No.: 12/412,577

(22) Filed: Mar. 27, 2009

(65) Prior Publication Data

US 2009/0192218 A1 Jul. 30, 2009

Related U.S. Application Data

(63) Continuation of application No. 10/556,199, filed as application No. PCT/EP2004/004768 on May 5, 2004, now abandoned.

(30) Foreign Application Priority Data

May 14, 2003 (EP) .................................... 03010804

(51) Int. Cl.
*A61K 31/34* (2006.01)
(52) U.S. Cl. ..................... 514/469; 514/470; 514/866
(58) Field of Classification Search ................. 514/469, 514/470, 866
See application file for complete search history.

(56) References Cited

U.S. PATENT DOCUMENTS

| 4,868,153 A | 9/1989 | Allison et al. |
| 2003/0165580 A1 | 9/2003 | Zhao |
| 2004/0081631 A1 | 4/2004 | Lee et al. |

FOREIGN PATENT DOCUMENTS

| CN | 1120953 A | 4/1996 |
| DE | 101 31 057 | 1/2003 |
| FR | 2 846 239 | 4/2004 |
| JP | 1 207233 | 8/1989 |
| WO | WO 95/00157 | 1/1995 |
| WO | WO 02/00638 A2 | 1/2002 |
| WO | WO 02/00638 A3 | 1/2002 |

OTHER PUBLICATIONS

Patent Abstracts of Japan, Section C, No. 655, vol. 13, No. 515, p. 70 (1989), English language abstract of JP 1 207233 A.
Derwent Database English language abstract of DE 101 31 057 A, WPI Accession No. 2004-110553/200412.
Derwent Database English language abstract of FR 2 846 239, WPI Accession No. 2004-347634/200432.
Chong, Z.Z. et al., "*Effect Of di-3-n-butylphthalide on the Activity of the Choline Acetyltransferase in Ischemic Brain and Cultured Neurons Subjected to Hypoglycemia/Hypoxie*," Chinese Pharmaceutical Journal, vol. 34, No. 8, pp. 519-522 (1999).
Ko, Wun-Chang, "A newly isolated antispasmodic-butylaidenephthalide", Japanese Journal of Pharmacology, Feb. 1980, vol. 30, No. 1, pp. 85-91.

*Primary Examiner* — Kevin E Weddington
(74) *Attorney, Agent, or Firm* — Hoxie & Associates, LLC

(57) ABSTRACT

The present invention relates to the use of a compound as effective agent for the prevention or treatment of diabetes mellitus in a mammal. Said compounds being selected from the group of phthalide derivatives and exhibit excellent blood glucose lowering effects and thus are effective agents in the prevention or treatment of diabetes mellitus in mammals.

9 Claims, No Drawings

USE OF PHTHALIDE DERIVATIVES FOR THE TREATMENT OF TYPE 2 DIABETES MELLITUS

CROSS REFERENCE TO RELATED APPLICATIONS

This application is a continuation of U.S. patent application Ser. No. 10/556,199, filed Sep. 11, 2006, now abandoned which is a 35 USC §371 application claiming benefit of PCT Application No. PCT/EP2004/004768 filed on May 5, 2004, which claims the benefit of EP Application No. 03010804.7 filed on May 14, 2003, the contents of each of which are incorporated herein by reference.

The present invention relates to the use of a compound as effective agent for the prevention or treatment of diabetes mellitus in a mammal. Said compounds being selected from the group of phthalide derivatives and are useful for the preparation of a pharmaceutical or a dietary composition given to a mammal in need thereof for the prevention or treatment of diabetes mellitus.

Diabetes mellitus defines a complex of metabolic diseases derived from multiple causative factors and is characterized by impaired carbohydrate, protein and fat metabolism associated with a deficiency in insulin secretion and/or insulin resistance. This results in elevated fasting and postprandial serum glucose that leads to complications if left untreated. Four different forms of diabetes mellitus are known, (1) type 1 diabetes mellitus, (2) type 2 diabetes mellitus, (3) the so-called gestational diabetes mellitus, which begins or is recognized for the first time during pregnancy, and (4) some other forms which are mainly based on genetic defects.

The two major forms of diabetes mellitus are the type 1 and type 2 diabetes mellitus, of which type 2 diabetes mellitus is the most prevailing form. Type 1 and type 2 diabetes mellitus are associated with hyperglycemia, hypercholesterolemia and hyperlipidemia. The insensitivity to insulin and absolute insulin deficiency in type 1 and 2 diabetes mellitus leads to a decrease in glucose utilization by the liver, muscle and the adipose tissue and to an increase in the blood glucose levels. Uncontrolled hyperglycemia is associated with increased and premature mortality due to an increased risk for microvascular and macrovascular diseases, including nephropathy, neuropathy, retinopathy, hypertension, stroke, and heart disease. Recent evidence showed that tight glycemic control is a major factor in the prevention of these complications in both type 1 and type 2 diabetes mellitus. Therefore, optimal glycemic control by drugs or therapeutic regimens is an important approach for the treatment of diabetes mellitus.

Type 1 diabetes mellitus is the form of diabetes mellitus which usually begins with childhood or puberty and is characterized by an auto-immune destruction of the insulin-producing β-cells leading to a complete deficiency of insulin secretion. Type 2 diabetes mellitus is the form of diabetes mellitus which occurs predominantly in adults in whom adequate production of insulin is available for use, yet a defect exists in insulin-mediated utilization and metabolism of glucose in peripheral tissues. The changes in various tissues associated with type 2 diabetes mellitus exist even before clinical symptoms are detected.

Therapy of type 2 diabetes mellitus initially involves dietary and lifestyle changes, when these measures fail to maintain adequate glycemic control the patients are treated with oral hypoglycemic agents and/or exogenous insulin. The current oral pharmacological agents for the treatment of type 2 diabetes mellitus include those that potentiate insulin secretion (sulphonylurea agents), those that improve the action of insulin in the liver (biguanide agents), insulin sensitizing agents (thiazolidinediones) and agents which act to inhibit the uptake of glucose in the gastrointestinal tract (α-glucosidase inhibitors). However, currently available agents generally fail to maintain adequate glycemic control in the long term due to progressive deterioration in hyperglycemia, resulting from progressive loss of pancreatic cell function. The proportion of patients able to maintain target glycemic levels decreases markedly overtime necessitating the administration of additional/alternative pharmacological agents. Furthermore, the drugs may have unwanted side effects and are associated with high primary and secondary failure rates.

It is known that the peroxisome proliferator-activated receptors (PPARs) play a critical physiological role as lipid sensors and regulators of lipid metabolism. The PPARs are activated to various degrees by high concentrations of long-chain fatty acids. Synthetic PPAR ligands, including the fibrates and thiazolidinediones, have proven effective in the treatment of dyslipidemia and diabetes mellitus, especially type 2 diabetes mellitus. Mostly, these compounds act with PPARγ, which is one isoform of the PPAR family, some of them are also able to interact with PPARα and/or PPARδ isoform.

Therefore, although the therapies of choice in the treatment of type 1 and type 2 diabetes mellitus are based essentially on the administration of insulin and of oral hypoglycemic drugs, there is a need for compounds with minimal side effects for the treatment and prevention of diabetes mellitus. Many patients are interested in alternative therapies which could minimize the side effects associated with high-dose of drugs and yield additive clinical benefits. Type 2 diabetes mellitus is a progressive and chronic disease, which usually is not recognized until significant damage has occurred to the pancreatic cells responsible for producing insulin and to the cardiovascular system. Therefore, there is also an increasing interest in the development of a dietary supplement that may be used to prevent the development of diabetes mellitus in people at risk especially in elderly who are at high risk for developing diabetes mellitus.

We now found that a group of known compounds exhibit excellent blood glucose lowering effects and thus are effective agents in the prevention or treatment of diabetes mellitus in mammals. These non-toxic compounds function as ligands for PPARγ. Therapeutic effects of these ligands include, but are not limited to, a decrease in the blood glucose level, prevention of obesity, a lowered insulin resistance, delay or prevention of type 2 diabetes mellitus and dyslipidemia, differentiation of adipocytes, lowered triglyceride levels, and normalized glucose tolerance.

The object of the present invention is the use of a compound represented by formula (I) as antidiabetic agent,

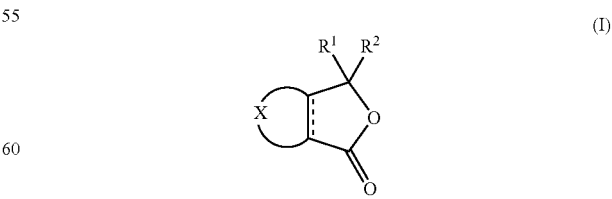

wherein
the dotted line is an optional bond;
$R^1$ is butyl or butyryl if $R^2$ is hydroxyl but is butyl if $R^2$ is hydrogen; or $R^1$ and $R^2$ taken together are 1-butylidene optionally substituted by hydroxyl, methyl, or 3-(α,β-dimethylacrylyloxy)-pentylidenyl;
X is a residue selected from the group consisting of X1, X2, X3, X4, and X5;

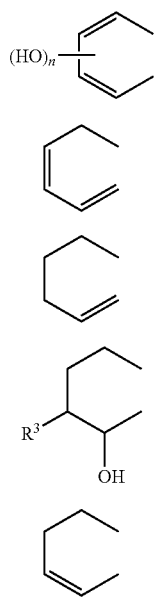

wherein
X is X2, X3 or X5 if the dotted line does not signify a bond in formula (I) above and X is X1, X4 or X5 if the dotted line signifies a bond in formula (I) above;
R³ is hydroxyl or butyryl; and
n is 1 or 2.

Thus, in a compound of formula (I) above X is X2, X3, or X5 in case of a tetrahydrofuran, i.e., if the dotted line in formula (I) does not signify a bond whereas X is X1, X4, or X5 in case of a dihydrofuran, i.e., if the dotted line in formula (I) signifies a bond.

The compounds according to formula (I) above as used herein may be also in the form of their pharmaceutically acceptable salts.

As used herein, the term "antidiabetic agent" means an agent which is capable of preventing or treating diabetes mellitus, especially type 2 diabetes mellitus, in a mammal which is in need thereof. These agents are also useful for the treatment or prevention of related symptoms.

The term "diabetes mellitus" also includes, but is not limited to, related symptoms such as increased blood glucose level, obesity, increased insulin resistance, hyperlipidemia, dyslipidemia, increase in cholesterol (hypercholesterinemia, hypertriglycerinemia), hyperinsulinemia, and impaired glucose tolerance. Impaired glucose tolerance and impaired fasting glucose are the two symptoms referred to as pre-diabetes mellitus. This stage is associated with the so-called insulin resistance syndrome also known as syndrome X. Since syndrome X is directly involved in the pathogenesis of type 2 diabetes mellitus, the compounds used for the present invention are also useful for the treatment or prevention of syndrome X.

An agonist of PPARγ relates to a small molecule interacting directly with PPARγ, particularly with its ligand binding domain, and thus activating the PPARγ.

The compounds as used for the present invention are selected from the group of phthalide derivatives, which refer to substituted lactones of 2-hydroxymethylbenzoic acid according to IUPAC Rule C-473. This class of compounds is based on 1(3H)-isobenzofuranone $C_8H_6O_2$.

Preferred compounds used as antidiabetic agents are selected from the group consisting of (E)-senkyunolide E; senkyunolide C; senkyunolide B; 3-butyl-4,5,6,7-tetrahydro-3,6,7-trihydroxy-1(3H)-isobenzofuranone; 3-butyl-1(3H)-isobenzofuranone; 3-butylphthalide; 3-butylidenephthalide; chuangxinol; ligustilidiol; senkyunolide F; 3-hydroxy-senkyunolide A; angeloylsenkyunolide F; senkyunolide M; 3-hydroxy-8-oxo-senkyunolide A; ligustilide; 6,7-dihydro-(6S,7R)-dihydroxyligustilide; 3a,4-dihydro-3-(3-methylbutylidene)-1(3H)-isobenzofuranone; sedanolide; and cnidilide. The most preferably used compounds are selected from the group consisting of ligustilide, 3-butylphthalide, 3-butylidenephthalide, and sedanolide. The preferred embodiments are listed in Table 1.

TABLE 1

List of preferred compounds used as antidiabetic agents

| Structure | Name |
| --- | --- |
| 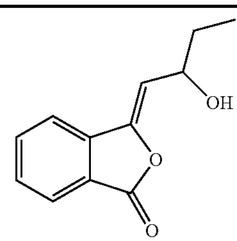 | (E)-Senkyunolide E |
| 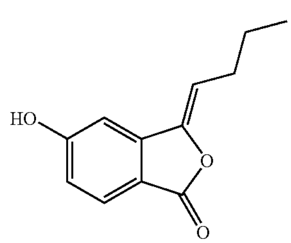 | Senkyunolide C |

TABLE 1-continued

List of preferred compounds used as antidiabetic agents

| Structure | Name |
| --- | --- |
| 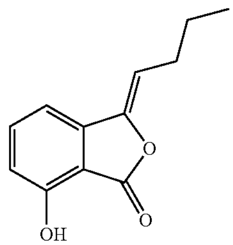 | Senkyunolide B |
| 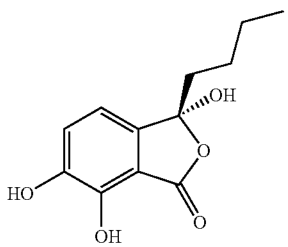 | 3-Butyl-4,5,6,7-tetrahydro-3,6,7-trihydroxy-1(3H)-isobenzofuranone |
| 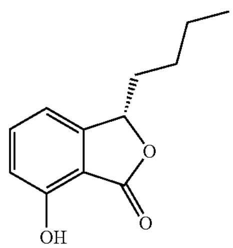 | 3-Butyl-1(3H)-isobenzofuranone |
| 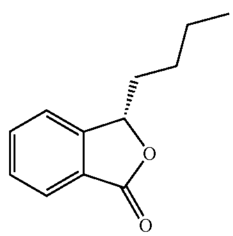 | 3-Butylphthalide |
| 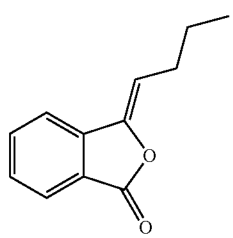 | 3-Butylidenephthalide |
| 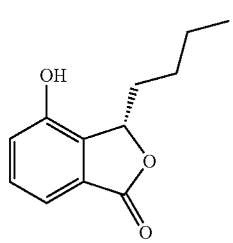 | Chuangxinol |

TABLE 1-continued

List of preferred compounds used as antidiabetic agents

| Structure | Name |
|---|---|
| 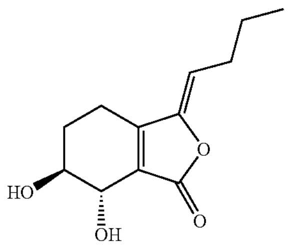 | Ligustilidiol |
| 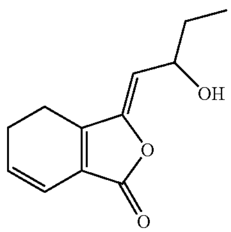 | Senkyunolide F |
| 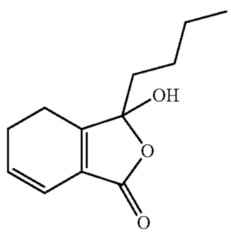 | 3-Hydroxy-senkyunolide A |
| 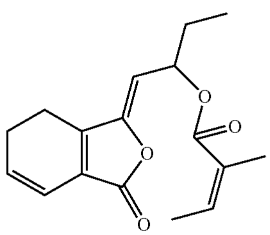 | Angeloylsenkyunolide F |
| 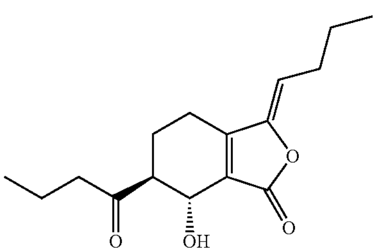 | Senkyunolide M |
| 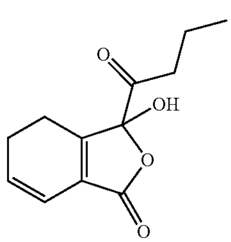 | 3-Hydroxy-8-oxo-senkyunolide A |

TABLE 1-continued

List of preferred compounds used as antidiabetic agents

| Structure | Name |
|---|---|
| 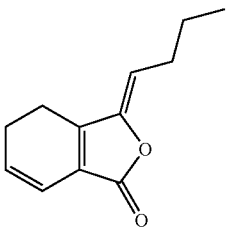 | Ligustilide |
| 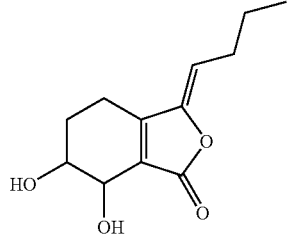 | 6,7-Dihyro-(6S,7R)-dihydroxyligustilide |
| 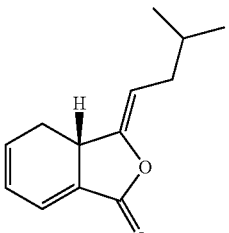 | 3a,4-Dihydro-3-(3-methylbutylidene)-1(3H)-isobenzofuranone |
| 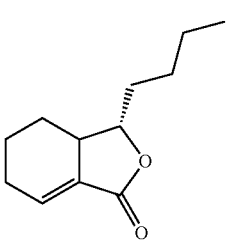 | Sedanolide |
| 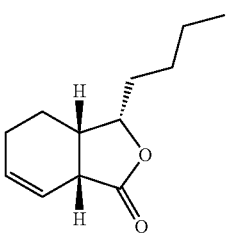 | Cnidilide |

Thus, it is an object of the present invention to use a compound which is selected from the group consisting of ligustilide, 3-butylphthalide, 3-butylidenephthalide, and sedanolide as antidiabetic agent.

The compounds according to formula (I) as defined above are used for the preparation of a pharmaceutical or dietary composition for the prevention or treatment of diabetes mellitus. Preferred compounds are represented in Table 1. The most preferably used compounds are selected from the group consisting of ligustilide, 3-butylphthalide, 3-butylidenephthalide, and sedanolide.

Another aspect of the present invention is the provision of a pharmaceutical or dietary composition for use in the treatment or prevention of diabetes mellitus comprising an effective amount of a compound of formula (I) as defined above. Preferred compounds are represented in Table 1. The most preferred compounds are selected from the group consisting of ligustilide, 3-butylphthalide, 3-butylidenephthalide, and sedanolide.

A pharmaceutical composition may further comprise pharmaceutically acceptable carriers, excipients or diluents, including, but not limited to, lubricants, colorants, wetting agents, fillers, disintegrants and flavorants.

A dietary composition may further comprise any known substances which are normally used and accepted in the preparation of such compositions.

The pharmaceutical or dietary composition may be in the form which is selected from the group consisting of fortified food or feed, beverages, tablets, granules, capsules, pastes, and effervescent formulations. The pastes may be filled into hard or soft gelatin capsules.

In one aspect, the present invention provides a method for the prevention or treatment of diabetes mellitus and in mammals, said method comprising:
(a) preparing a composition comprising a compound according to formula (I) as defined above, and
(b) administering an effective dose of said composition to a mammal which is in need thereof.

As used herein, an "effective dose" of the compounds of the present invention is an amount which is high enough to effect activation of PPARγ and thus lowering the blood glucose level in a mammal. A suitable dose is within the range of about 0.01 to about 50 mg/kg body weight/day.

The compounds according to formula (I) as defined above and which are used as antidiabetic agents may be isolated by methods known in the art [see, e.g., Beck J. J. and Stermitz F. R., J. Natural Products, Vol. 58, No. 7, pp. 1047-1055, 1995] from various plants such as *Angelica glauca, Angelica acutiloba, Angelica sinensis, Angelicae dahuricae, Ligusticum acutilobum, Ligusticum officinale, Ligusticum sinense, Ligusticum wallichii, Cnidium officinale, Rhizoma Chuanxiong, Pleurospermum hookeri, Trachyspermum roxburghianum, Meum athamanticum, Lomatium torreyi, Scutellaria baicalensis, Opopanax chironium, Cenolophium denudatum, Coriandrum sativuum, Silaum silaus*. The compounds used herein may also be of synthetic origin. It is understood that all compounds as used herein are in pure form.

EXAMPLE 1

Effect of Ligustilide on Glucose Uptake of Adipocytes

Unless otherwise stated, the ligustilide as used herein was purchased from GAIA Chemical Corporation, 23 George Washington Plaza, Gaylorsville, Conn. 06755, USA and has a purity of about 95% (purified by column chromatography).

C3H10T1/2 cells (ATCC CCL-226) were grown for 5 days to confluence in DMEM supplemented with 10% FBS medium and induced with a mixture of insulin, dexamethasone and 3-isobutyl-1-methylxanthine to differentiate into adipocytes. Nine days after the beginning of induction, cells were treated for 48-h with ligustilide at different concentrations as shown in Table 2. Glucose uptake was determined using radioactive 2-deoxyglucose (10 µM 2-DG in HBS+0.5 µCi/ml of 3[H]-2-DG), measuring glucose uptake in the absence of insulin. Basal glucose uptake was increased by 48-h treatment with ligustilide in a dose-dependent manner (Table 2). This increase in glucose uptake was specific, since the increase was not observed in the presence of phloretin, a known inhibitor of specific glucose uptake. As a positive control, the known PPARγ agonist ciglitazone was used in the concentration as indicated in Table 2.

EXAMPLE 2

Effect of 3-Butylphthalide on Glucose Uptake of Adipocytes

Unless otherwise stated, the 3-butylphthalide as used herein was purchased from Advanced Synthesis Technologies, P.O. Box 437920, San Ysidro, Calif. 92173, USA.

Growing, induction and treatment of C3H10T1/2 cells were exactly as described in Example 1, with die exception that 3-butylphthalide at different concentrations was used instead of ligustilide. An increase of basal glucose uptake could be detected as shown in Table 2.

EXAMPLE 3

Effect of 3-Butylidenephthalide on Glucose Uptake of Adipocytes

Unless otherwise stated, the 3-butylidenephthalide as used herein was purchased from Aldrich Chemical Company, Inc., 1001 West Saint Paul Avenue, Milwaukee, Wis. 53233, USA and has a purity of >96%.

Growing, induction and treatment of C3H10T1/2 cells were exactly as described in Example 1, with the exception that 3-butylidenphthalide at different concentrations was used instead of ligustilide. As shown in Table 2, an increase of the basal glucose uptake could be detected.

TABLE 2

Induction of glucose uptake by 48-h treatment with different compounds (% of control ± SEM)

| Compound | Concentration [M] | Basal glucose uptake |
| --- | --- | --- |
| Ciglitazone | $5 \times 10^{-5}$ | 381.5 ± 24.4 |
| Ligustilide | $5 \times 10^{-6}$ | 105.9 ± 24.4 |
|  | $5 \times 10^{-5}$ | 131.8 ± 24.4 |
|  | $1 \times 10^{-4}$ | 175.0 ± 24.4 |
|  | $2 \times 10^{-4}$ | 294.4 ± 24.4 |
| 3-Butylphthalide | $1 \times 10^{-6}$ | 99.3 ± 8.5 |
|  | $1 \times 10^{-5}$ | 97.5 ± 8.5 |
|  | $1 \times 10^{-4}$ | 136.7 ± 8.5 |
| 3-Butylidenephthalide | $1 \times 10^{-6}$ | 107.0 ± 8.5 |
|  | $1 \times 10^{-5}$ | 123.8 ± 8.5 |
|  | $1 \times 10^{-4}$ | 137.3 ± 8.5 |

Control: C3H10T1/2 cells treated for 48 h with DMSO at the same concentration as compound-treated cells and set at 100%

EXAMPLE 4

Effect of Ligustilide on Differentiation of Adipocytes

C3H10T1/2 cells were grown to confluence as described in Example 1, then treated for 10 days with insulin alone (negative control) or with a mixture of insulin and ligustilide at different concentrations (see Table 3), with re-feeding with fresh medium and compounds every 48-h. After the 10-day treatment, the cells were stained with oil Red O as follows: cells were washed 2× in PBS and fixed in 10% formalin at room temperature for 1 h. After removal of formalin, 200 µl of oil Red O staining solution (3:2 mixture of 0.5% w/v oil Red O stock solution and water) was applied to each well. The cells were incubated for 20 min at room temperature, washed twice in 2×PBS and incubated for 10 min with 300 µl of isopropanol/well for oil Red O extraction. Quantification of oil Red O was determined by measuring absorbance at 540 nm (mean OD). Co-treatment of C3H10T1/2 cells with insulin and ligustilide resulted in a higher differentiation of the cells into adipocytes than insulin alone as represented by a higher amount of oil Red O staining (Table 3).

TABLE 3

Induction of adipocyte differentiation
by 10-day treatment with ligustilide

| Compound | Mean OD ± SEM |
|---|---|
| Insulin ($2 \times 10^{-7}$ M) | 0.687 ± 0.34 |
| Insulin ($2 \times 10^{-7}$ M) + ligustilide ($5 \times 10^{-6}$ M) | 1.71 ± 0.34 |

EXAMPLE 5

Effect of 3-Butylphthalide on Differentiation of Adipocytes

C3H10T1/2 cells were grown and treated as described in Example 4 with the exception that 3-butylphthalide was used instead of ligustilide. The measurement of adipocyte differentiation using the oil Red O assay was performed as described in Example 4. Co-treatment of C3H10T1/2 cells with insulin and 3-butylphthalide resulted in a higher differentiation of the cells into adipocytes than insulin alone (Table 4).

TABLE 4

Induction of adipocyte differentiation by 10-day treatment
with 3-butylphthalide or 3-butylidenephthalide

| Compound | Mean OD ± SEM |
|---|---|
| Insulin ($1 \times 10^{-7}$ M) | 0.14 ± 0.01 |
| Insulin ($1 \times 10^{-7}$ M) + 3-butylphthalide ($1 \times 10^{-5}$ M) | 0.21 ± 0.01 |
| Insulin ($1 \times 10^{-7}$ M) + 3-butylidenephthalide ($1 \times 10^{-5}$ M) | 0.15 ± 0.01 |
| Insulin ($1 \times 10^{-7}$ M) + 3-butylidenephthalide ($5 \times 10^{-5}$ M) | 0.22 ± 0.01 |
| Insulin ($1 \times 10^{-7}$ M) + 3-butylidenephthalide ($1 \times 10^{-4}$ M) | 0.28 ± 0.01 |

EXAMPLE 6

Effect of 3-Butylidenephthalide on Differentiation of Adipocytes

C3H10T1/2 cells were grown and treated as described in Example 4 with the exception that 3-butylidenephthalide was used instead of ligustilide. The measurement of adipocyte differentiation using the oil Red O assay was performed as described in Example 4. Co-treatment of C3H10T1/2 cells with insulin and 3-butylidenephthalide resulted in a higher differentiation of the cells into adipocytes than insulin alone (Table 4).

EXAMPLE 7

Effect of Sedanolide on Differentiation of Adipocytes

Unless otherwise stated, the 3-butylphthalide as used herein was purchased from Sigma, P.O. Box 14508, St Louis, Mo. 63178, USA and has a purity of about >98%.

C3H10T1/2 cells were grown and treated as described in Example 4 with the exception that sedanolide was used instead of ligustilide. The measurement of adipocyte differentiation using the oil Red O assay was performed as described in Example 4. Co-treatment of C3H10T1/2 cells with insulin and sedanolide resulted in a higher differentiation of the cells into adipocytes than insulin alone (Table 5).

TABLE 5

Induction of adipocyte differentiation
by 10-day treatment with sedanolide

| Compound | Mean OD ± SEM |
|---|---|
| Insulin ($1 \times 10^{-7}$ M) | 0.16 ± 0.01 |
| Insulin ($1 \times 10^{-7}$ M) + sedanolide ($1 \times 10^{-5}$ M) | 0.15 ± 0.01 |
| Insulin ($1 \times 10^{-7}$ M) + sedanolide ($1 \times 10^{-4}$ M) | 0.18 ± 0.01 |

EXAMPLE 7

Effect of Ligustilide on Glucose Tolerance

The efficacy of ligustilide on glucose tolerance was tested in a 7-day study in C57BLKS/J db/db mice (n=10/group), a model of late type 2 diabetes mellitus with severe hyperglycemia which is widely used to determine the efficacy of PPARγ ligands.

Male db/db mice were obtained from Jackson Laboratory (Bar Harbor, Me., USA). Adult mice aged 12 weeks were used in the experiment. Mice were housed individually in plastic cages with bedding and allowed free access to standard rodent food and tap water. The animal rooms were controlled for temperature (24° C.), humidity (55%), and light (12-h light-dark cycle). The animals were randomized in two groups and ligustilide was administered orally to one of the groups for 7 days at a dose of 200 mg/kg BW/day. After 7 days of treatment the concentration of glucose was determined in blood from fed animals, i.e., animals which were not restricted from food. After a period of 5 days of treatment an oral glucose tolerance test (OGTT) was performed. For the OGTT mice were fasted overnight and then a 1-g glucose/kg BW solution was orally administered. Blood samples were taken before and 15, 30, 45, 60, 90, 120, 150, 180 min after the glucose challenge for determination of blood glucose levels and then the area under the curve (AUC) was determined. Blood glucose was measured by a glucose analyzer (Glucotrend Premium, Roche Diagnostics, Rotkreuz, Switzerland). The blood glucose levels and AUC for the OGTT measurement are given in Table 6. The glucose levels of fed animals (see above) were significantly lowered after 7 days of ligustilide treatment. After 5 days of ligustilide treatment the glucose levels of fasted animals, i.e., animals with an overnight fasting (see above) were significantly decreased as compared to the untreated control group. During the OGTT test the blood glucose levels in the ligustilide treated animals were lower at all time points when compared with the control group. Thus, ligustilide significantly reduced the glucose AUC of an OGTT (1 g glucose/kg body weight) on day 5.

TABLE 6

Blood glucose level in db/db mice treated with ligustilide

| | Blood Glucose | | Glucose |
|---|---|---|---|
| | Fasted (mg/dl) | Fed (mg/dl) | AUC |
| Control | 233 | 503 | 69340 |
| Ligustilide (200 mg/kg BW/day) | 196 | 388 | 51039 |

The invention claimed is:

1. A method of treating type 2 diabetes mellitus in mammals comprising:
   administering to a mammal an effective dose of compound represented by formula (I),

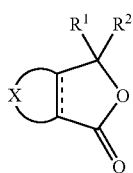

(I)

wherein
   the dotted line is an optional bond;
   $R^1$ is butyl or butyryl if $R^2$ is hydroxyl but is butyl if $R^2$ is hydrogen; or $R^1$ and $R^2$ taken together are 1-butylidene optionally substituted by hydroxyl, methyl, or 3-(α,β-dimethylacrylyloxy)-pentylidenyl;
   X is a residue selected from the group consisting of X1, X2, X3, X4, and X5;

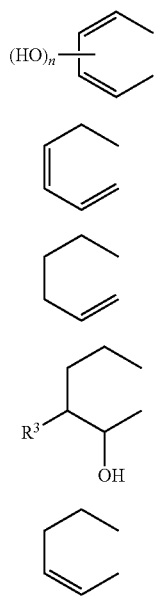

wherein
   X is X2, X3 or X5 if the dotted line does not signify a bond in formula (I) above and X is X1, X4 or X5 if the dotted line signifies a bond in formula (I) above;
   $R^3$ is hydroxyl or butyryl; and
   n is 1 or 2
   in free of pharmaceutically acceptable salt form.

2. A method according to claim 1 wherein the compound is selected from the group consisting of (E)-senkyunolide E; senkyunolide C; senkyunolide B; 3-butyl-4,5,6,7-tetrahydro-3,6,7-trihydroxy-1(3H)-isobenzofuranone; 3-butyl-1(3H)-isobenzofuranone; 3-butylphthalide; 3-butylidenephthalide; chuangxinol; ligustilidiol; senkyunolide F; 3-hydroxy-senkyunolide A; angeloylsenkyunolide F; senkyunolide M; 3-hydroxy-8-oxo-senkyunolide A; ligustilide; 6,7-dihydro-(6S,7R)-dihydroxyligustilide; 3a,4-dihydro-3-(3-methylbutylidene)-1(3H)-isobenzofuranone; sedanolide; and cnidilide in free of pharmaceutically acceptable salt form.

3. The method of claim 1, wherein the compound of formula (I) is ligustilide in free or pharmaceutically acceptable salt form.

4. A method for treatment of type 2 diabetes mellitus in mammals, said method comprising:
   (a) preparing a composition comprising an effective amount of a compound of formula (I),

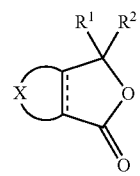

(I)

wherein
   the dotted line is an optional bond;
   $R^1$ is butyl or butyryl if $R^2$ is hydroxyl but is butyl if $R^2$ is hydrogen; or $R^1$ and $R^2$ taken together are 1-butylidene optionally substituted by hydroxyl, methyl, or 3-(α,β-dimethylacrylyloxy)pentylidenyl;
   X is a residue selected from the group consisting of XI, X2, X3, X4, and X5;

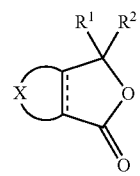

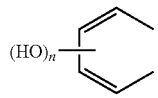

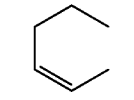

wherein
   X is X2, X3 or X5 if the dotted line does not signify a bond in formula (I) above and X is X1, X4 or X5 if the dotted line signifies a bond in formula (I) above;
   $R^3$ is hydroxyl or butyryl; and
   n is 1 or 2,
   in free or pharmaceutically acceptable salt form; and
   (b) administering an effective dose of said composition to a mammal which is in need thereof.

5. A method according to claim 4 wherein the compound of formula 1 is selected from the group consisting of (E)-senkyunolide E; senkyunolide C; senkyunolide B; 3-butyl-4,5,6,7-tetrahydro-3,6,7-trihydroxy-1(3H)-isobenzofuranone;

3-butyl-1(3H)-isobenzofuranone; 3-butylphthalide; 3-butylidenephthalide; chuangxinol; ligustilidiol; senkyunolide F; 3-hydroxy-senkyunolide A; angeloylsenkyunolide F; senkyunolide M; 3-hydroxy-8-oxo-senkyunolide A; ligustilide; 6,7-dihydro-(6S,7R)-dihydroxyligustilide; 3a,4-dihydro-3-(3-methylbutylidene)-1(3H)-isobenzofuranone; sedanolide; and cnidilide in free or pharmaceutically acceptable salt form.

6. A method according to claim 4 wherein the compound of formula 1 is selected from the group consisting of ligustilide, 3-butylphthalide, 3-butylidenephthalide, and sedanolide in free or pharmaceutically acceptable salt form.

7. A method according to claim 4 wherein the composition further comprises a pharmaceutically acceptable carrier, excipient, or diluent.

8. A method according to claim 4 wherein the composition is in a form selected from the group consisting of a fortified food or feed, a beverage, a tablet, a granule, a capsule, a paste, and an effervescent formulation.

9. The method of claim 4, wherein the compound of formula (I) is ligustilide in free or pharmaceutically acceptable salt form.

* * * * *